(12) United States Patent
Reevell

(10) Patent No.: US 11,478,590 B2
(45) Date of Patent: Oct. 25, 2022

(54) AEROSOL GENERATING DEVICE WITH SPIRAL MOVEMENT FOR HEATING

(71) Applicant: PHILIP MORRIS PRODUCTS S.A., Neuchâtel (CH)

(72) Inventor: Tony Reevell, London (GB)

(73) Assignee: Philip Morris Products S.A., Neuchâtel (CH)

(*) Notice: Subject to any disclaimer, the term of this patent is extended or adjusted under 35 U.S.C. 154(b) by 208 days.

(21) Appl. No.: 16/623,581

(22) PCT Filed: Jul. 18, 2018

(86) PCT No.: PCT/IB2018/055358
§ 371 (c)(1),
(2) Date: Dec. 17, 2019

(87) PCT Pub. No.: WO2019/016740
PCT Pub. Date: Jan. 24, 2019

(65) Prior Publication Data
US 2021/0145057 A1    May 20, 2021

(30) Foreign Application Priority Data
Jul. 21, 2017 (EP) .................... 17182691

(51) Int. Cl.
*A24F 40/46* (2020.01)
*A61M 11/04* (2006.01)
(Continued)

(52) U.S. Cl.
CPC ............. *A61M 11/042* (2014.02); *A24D 1/20* (2020.01); *A24F 40/40* (2020.01); *A24F 40/46* (2020.01);
(Continued)

(58) Field of Classification Search
CPC ....... A61M 11/042; A24F 40/20; A24F 40/40; A24F 40/46; A24D 1/20
See application file for complete search history.

(56) References Cited

U.S. PATENT DOCUMENTS 5,269,327 A    12/1993    Counts et al.
5,301,666 A    4/1994    Lerk et al.
(Continued)

FOREIGN PATENT DOCUMENTS

EP    0758532 B1    10/2002
EP    1522325 A1    4/2005
(Continued)

OTHER PUBLICATIONS

Russian Office Action for RU2019142706 issued by the Patent Office of the Russian Federation; dated Oct. 20, 2021; 10 pgs. including English translation.
(Continued)

*Primary Examiner* — Hae Moon Hyeon
(74) *Attorney, Agent, or Firm* — Mueting Raasch Group

(57) ABSTRACT

An aerosol generating device includes a housing having an open end and forms a cavity in communication with the open end for receiving an aerosol generating article. The device further includes a rotatable capture element disposed in the cavity. The rotatable capture element is operable to retain the aerosol generating article within the cavity. The rotatable capture element is longitudinally movable within the cavity. The device further includes a heating element in communication with the cavity. The heating element is operable to heat the aerosol generating article retained by the capture element within the cavity. Combined rotation and longitudinal movement of the capture element causes the aerosol generating element to spiral relative to the heating element.

15 Claims, 5 Drawing Sheets

(51) Int. Cl.
*A24D 1/20* (2020.01)
*A24F 40/40* (2020.01)
*A24F 40/60* (2020.01)
*H05B 3/42* (2006.01)
*A24F 40/20* (2020.01)

(52) U.S. Cl.
CPC ............... *A24F 40/60* (2020.01); *H05B 3/42* (2013.01); *A24F 40/20* (2020.01)

(56) References Cited

U.S. PATENT DOCUMENTS

| | | | |
|---|---|---|---|
| 5,649,554 | A | 7/1997 | Sprinkel et al. |
| 5,769,073 | A | 6/1998 | Eason et al. |
| 6,053,176 | A * | 4/2000 | Adams .................... A24F 40/60 131/329 |
| 7,415,982 | B1 | 8/2008 | Sheridan |
| 9,532,603 | B2 | 1/2017 | Plojoux et al. |
| 9,693,587 | B2 | 7/2017 | Plojoux et al. |
| 10,375,991 | B2 | 8/2019 | Lipowicz |
| 2013/0037041 | A1 | 2/2013 | Worm et al. |
| 2014/0338686 | A1 | 11/2014 | Plojoux et al. |
| 2015/0013696 | A1 | 1/2015 | Plojoux et al. |
| 2016/0088874 | A1 | 3/2016 | Lipowicz |
| 2018/0177958 | A1 * | 6/2018 | Wilder .................... A24F 40/48 |
| 2020/0154768 | A1 * | 5/2020 | Han ........................ A24F 40/46 |

FOREIGN PATENT DOCUMENTS

| | | | |
|---|---|---|---|
| KR | 20130035670 A | | 4/2013 |
| RU | 2604012 | | 12/2016 |
| WO | WO 2009/077244 A1 | | 6/2009 |
| WO | WO 2015/082654 A1 | | 6/2015 |
| WO | WO 2015/155289 A1 | | 10/2015 |
| WO | WO-2015155289 A1 * | 10/2015 | ............. A24F 40/46 |
| WO | 20150177255 | | 11/2015 |

OTHER PUBLICATIONS

European Search Report for EP Application No. 17182691.0, issued by the European Patent Office dated Nov. 6, 2017; 7 pgs.
International Search Report and Written Opinion for PCT/IB2018/055358, issued by the European Patent Office dated Nov. 15, 2018; 15 pgs.
International Preliminary Report on Patentability for PCT/IB2018/055358, issued by the International Bureau of WIPO dated Jan. 30, 2020; 9 pgs.
European Search Report issued for EP 18755321.9, issued by the European Patent Office dated Nov. 10, 2020; 8 pgs.
Japanese Office Action for JP 2019-571387 issued by the Japanese Patent Office dated Aug. 29, 2022; 3 pgs.

* cited by examiner

AEROSOL GENERATING DEVICE WITH SPIRAL MOVEMENT FOR HEATING

RELATED APPLICATIONS

This application is the § 371 U.S. National Stage of International Application No. PCT/IB2018/055358, filed 18 Jul. 2018, which claims the benefit of European Application No. 17182691.0, filed 21 Jul. 2017.

INTRODUCTION

The present disclosure relates to aerosol generating devices for use with aerosol generating articles having an aerosol generating substrate, or "consumable", such as a tobacco substrate. Preferably, such a device is configured to sufficiently heat the substrate to cause generation of an aerosol, without combusting the substrate. These are known as "heat-not-burn" devices.

A consumable comprising an aerosol generating substrate may be heated in a number of suitable ways to cause aerosol generation. The devices may contain a single heater or multiple heaters. The use of a single heater may be advantageous because it may require less space and may allow the device to be smaller. The device may also be less expensive to produce and easier to maintain if the device contains a single heater rather than multiple heaters.

The consumable may be heated by the device internally or externally. One commercially available internal heating, heat-not-burn, device is the Philip Morris International IQOS heating device, which heats Heatstick tobacco-containing articles that resemble conventional cigarettes. The IQOS heating device includes a heating blade that pierces the Heatstick to contact and heat the tobacco substrate. A user may draw on a mouth end of the Heatstick to cause aerosol flow through the Heatstick for inhalation. Because the substrate is not combusted, by-products of combustion and pyrolysis are not included in the aerosol, and thus are not delivered to the user for inhalation Other devices for externally heating tobacco-containing consumables for combustion, or for heating without combustion, have been described. It is desirable in heat-not-burn devices to include means to ensure that a large proportion of the substrate is heated. It may be desirable to do this with a small, single heater. Mechanisms attempting to achieve this have been described. For example, published patent application US 2013/037041 A1 describes a device where a consumable is longitudinally advanced past a heater; and U.S. Pat. No. 6,053,176 A describes a device where a consumable is rotated relative to a heater.

While a number of devices have been proposed for heating aerosol generating substrate or articles containing an aerosol generating substrate, it would be desirable to produce a device that can heat an aerosol generating substrate in an efficient manner. It would also be desirable to heat the substrate without substantial waste of substrate.

SUMMARY

In various aspects of the present invention there is provided an aerosol generating device for heating an aerosol generating article comprising an aerosol generating substrate. The device comprises a housing having an open end and forms a cavity in communication with the open end for receiving the aerosol generating article. The device further comprises a rotatable capture element disposed in the cavity. The rotatable capture element is operable to physically restrain the aerosol generating article when the aerosol generating article is inserted into the cavity. The rotatable capture element is longitudinally movable within the cavity. The device further comprises a heating element in communication with the cavity. The heating element is operable to heat the aerosol generating article when the aerosol generating article is inserted into the cavity and restrained or retained by the capture element.

Rotation of the capture element when the aerosol generating article is restrained in the capture element causes the aerosol generating element to rotate relative to the heating element. Preferably, rotation of the capture element also causes the capture element to move longitudinally in the cavity. Accordingly, rotation of the capture element may cause spiral movement of the aerosol generating article retained by the capture element relative to the heater. Preferably, the movement of the capture element is indexed relative to the heater. That is to say, preferably the capture element, and therefore the aerosol generating article, is movable in steps or increments relative to the heater. Preferably the capture element is configured to move in increments of a predetermined amount. Each step, or predetermined increment, that the capture element moves exposes a new portion of the aerosol generating article to the heater. The size of the steps or increments may be chosen such that each new portion of the aerosol generating article is adjacent, but not overlapping, with a portion of the article heated by the heater in the preceding step. The rotation of the capture element allows each new portion to be displaced from the preceding portion around the circumference of the aerosol generating article. The longitudinal movement of the capture element allows each new portion to be displaced from the preceding portion along the length of the aerosol generating article. The combination of the rotation and longitudinal movement of the capture element creates spiral movement. The spiral movement of the capture element may be such that one full rotation of the capture element coincides with longitudinal displacement at least as long as the length of each heated portion, such that the heated portions do not overlap. The heater element heats adjacent portions of the aerosol generating article in sequence.

Various aspects or embodiments of the aerosol generating devices described herein may provide one or more advantages relative to currently available or previously described aerosol generating devices. For example, one or more aerosol generating devices described herein may use a relatively small heating element, which may provide space and energy efficiency. By using a small heating element, the amount of energy required to heat the element to a sufficient temperature to cause aerosol generation may be reduced relative to devices employing larger heating elements. In addition, the use of a smaller heating element may allow for heating of a smaller portion of the article containing the aerosol generating substrate, which may reduce wasteful depletion of the substrate. That is, targeted heating of the substrate preferably depletes only a portion of the substrate sufficient to produce sufficient aerosol for a given puff or number of puffs before movement of the article within the device such that a fresh portion of the aerosol generating substrate is heated for aerosol production. Thus, in at least some aspects, the aerosol generating devices may provide for energy efficiency and efficient depletion of the aerosol generating substrate of aerosol generating articles used with the devices. Further, spiral movement of the aerosol generating article within the device may allow the heater to heat a large proportion of the surface area of the substrate in sequential steps. The heater may incrementally "track out" a greater surface area for heating the substrate, resulting in more complete depletion of the substrate, and may be useful when additional puffs are desired, relative to, for example, mere rotational or longitudinal movement.

DETAILED DESCRIPTION

Figure 1:
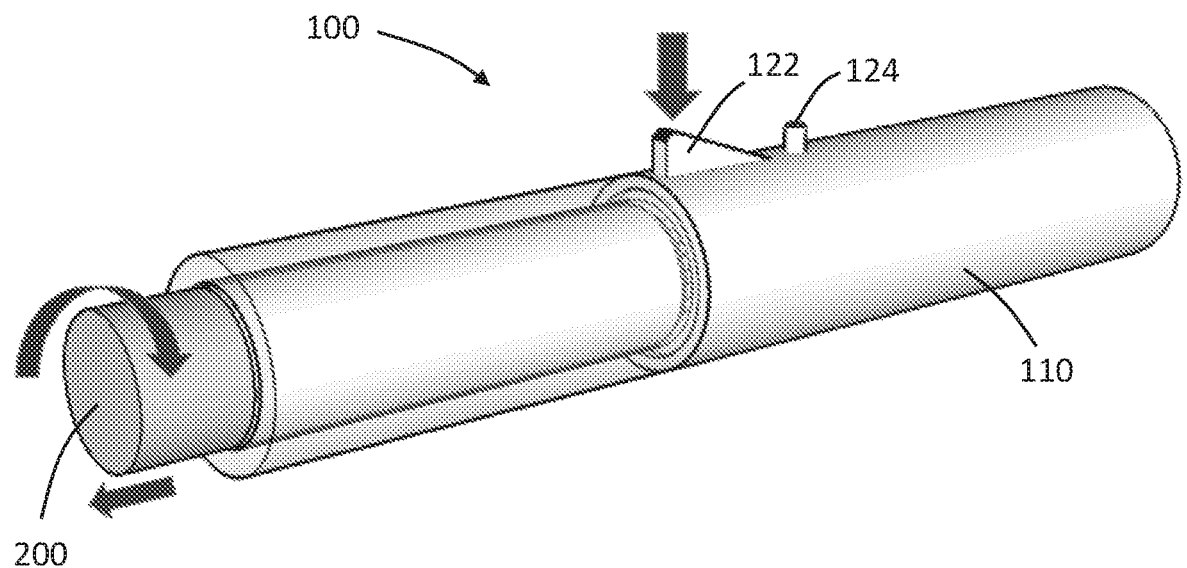
FIG. 1 is a schematic perspective view of an aerosol generating article retained within an aerosol generating device of the present invention.

An aerosol generating device according to an aspect of the present invention comprises a housing having an open end and forms a cavity in communication with the open end. A consumable aerosol generating article, such as a rod-shaped article, may be inserted into the cavity through the open end of the device. A portion of the article may protrude from the open end of the cavity and may serve as a mouthpiece, through which a user may inhale generated aerosol.

The device comprises a heating element in, or exposed to, the cavity. When the article is inserted in the cavity, the heating element is positioned adjacent to the article and may heat aerosol generating substrate of the article to cause generation of an aerosol, that may be inhaled through the mouth end of the article by a user. The heating element may be positioned adjacent the aerosol generating article and may heat the aerosol generating substrate from outside the article. The heating element may be in direct contact with the aerosol generating article. The heating element may be spaced apart from the aerosol generating article. A portion of the housing may separate the heating element from the aerosol generating article. The heating element may be adjacent only a portion of the available outer surface of the article and may therefore only heat and produce aerosol for a portion of the article. The heated section or portion becomes a "used section" or "used portion".

Once a section of the aerosol generating article has been heated and used, the aerosol generating article may be moved into a different position to expose a fresh and unused section of tobacco which may then be heated. This process may continue until the article has been exhausted or until further advancement of the article would not result in heating of a fresh and unused portion of the article.

Preferably, the device provides a way to index the consumable aerosol generating article relative to the heater. For example, the aerosol generating article may be secured at a distal end to capture element that is rotatable and longitudinally advanceable in the device cavity such that after a section of the aerosol generating article has been used, the article may be rotated and moved longitudinally, to expose a fresh unused section of the article for heating.

An aerosol generating device according to the present invention may comprise any suitable housing. The housing may comprise one or more parts. The housing may define an outer surface of the device. The housing has an open end and forms a cavity in communication with the open end for receiving an aerosol generating article.

The housing may be made from any one or more suitable materials. For example, the housing may comprise one or more of a metallic material, a glass material, and a thermoplastic material.

The housing may have any suitable dimensions. Preferably, the housing has dimensions similar to a conventional cigarette or cigar. As used herein, "diameter" refers to a maximum distance across a transverse section. The cross-sectional shape of the housing is preferably circular, but may have any other suitable shape. The housing may have an outer diameter in a range from about 3 mm to about 30 mm. Preferably, the housing has an outer diameter in a range from about 5 mm to about 25 mm, such as from about 5 mm to about 20 mm, or from about 6 mm to about 14 mm. More preferably, the housing has an outer diameter in a range from about 6 mm to about 10 mm.

The outer diameter of the housing may vary along the length of the housing. Preferably, the outer diameter of the housing is substantially uniform along the length of the housing. The outer diameter of the housing may be substantially uniform except for a number of projections or buttons on the outer surface.

The housing of the aerosol generating substrate may have any suitable length. Preferably, the housing has a length in a range from about 30 mm to about 150 mm, such as from about 20 mm to about 120 mm, or from about 45 mm to about 110 mm. More preferably, the housing as a length in a range from about 50 mm to about 100 mm.

The housing may have any suitable shape. Preferably, the housing has a substantially cylindrical exterior shape.

The cavity formed by the housing may have any suitable dimensions and shape. Preferably, the cavity has a diameter only slightly larger than the outer diameter of the aerosol generating article that the cavity is configured to receive. For example, the diameter of the cavity, as well as the open end of the housing, may be in a range from about 0.1 mm to about 0.5 mm larger than the outer diameter of the aerosol generating article.

Any suitable capture element may be disposed in the cavity of the housing. The capture element physically retains the aerosol generating article in the cavity after insertion. The capture element may prevent accidental removal of the aerosol generating article from the cavity. The capture element may contain barbs configured to penetrate into the article to retain the article, may contain inwardly biased deflectable elements that deflect outwardly when the article is inserted and retain the article due to the inward biasing force, or may contain any other suitable article retention members or combinations thereof.

The aerosol generating article may comprise a feature configured to cooperate with a feature of the capture element to retain the aerosol generating article relative to the capture element. For example, the aerosol generating article may comprise a plate at an end opposite the mouth end. The plate may comprise a feature configured to cooperate with a feature of the capture element. For example, the plate may comprise indents or holes through the plate configured to mate with detents or projections of the capture element. The plate may be incorporated into the aerosol generating article by a manufacturer of the article, or may be placed on the end of the article by a consumer.

The capture element is rotatable within the cavity and is longitudinally movable within the cavity. Following heating and use of a particular portion of the aerosol generating article, the capture element may rotate and longitudinally advance in the cavity to allow heating of a fresh, unused portion of the article.

The capture element may be coupled to a shaft within the cavity. The shaft may be rotatable within the cavity. Rotation of the shaft may cause rotation of the capture element. Longitudinal movement of the shaft may cause longitudinal movement of the capture element. Combined rotation and longitudinal movement of the shaft may cause spiral movement of the capture element.

The shaft may comprise a thread and the device may comprise thread engagement element configured to engage the thread of the shaft. Rotation of the shaft while the thread is engaged by the thread engagement element may cause the capture element to rotate and longitudinally advance in a spiral manner within the cavity formed by the housing of the device.

The pitch of the thread is preferably matched to the size of the heating element. In this way one full rotation of the capture element results in longitudinal advancement by a distance equal to the length of the heating element. Preferably, the thread is configured such that in operation rotation of the capture element results in longitudinal advancement proximally, towards the open end of the cavity. In this way, as the aerosol generating article is sequentially heated, it is also moved incrementally further out of the cavity. In alternative embodiments, the thread could be configured to advance the aerosol generating article in the opposite direction during use, such that it is moved incrementally further into the cavity.

The thread engagement element may be actuatable to disengage the thread and to allow the shaft to be pushed distally into the cavity if the shaft has advanced proximally through the cavity. For example, the thread engagement element may be coupled to a user activatable button. The user may actuate the button to disengage the thread engagement element. Actuating the button may allow the shaft and capture element to be moved manually within the cavity. This button may be termed a "disengaging button".

Preferably, before use, the capture element is located proximally within the cavity, adjacent to the open end. An aerosol generating article can be attached to the capture element by inserting the aerosol generating article into the open end of the cavity. Once the aerosol generating article is retained on the capture element, the aerosol generating article and capture element together can be pushed distally into the cavity. For example, by inserting an aerosol generating article into the cavity and pushing against the capture element, both the capture element and the aerosol generating article can be pushed until the shaft and capture element are reset to a starting position in the cavity. Disengagement or de-actuation of the button preferably results in the thread engagement element re-engaging the thread of the shaft. During use the capture element is moved spirally in a proximal direction, towards the open end of the cavity.

In an alternative embodiment, an aerosol generating article is inserted into the open end of the cavity when the capture element is located at a distal end of the cavity, set away from the open end. In this embodiment, the button is actuated to disengage the thread engagement element and the capture element attached to the aerosol generating article are moved towards the open end of the cavity. During use the capture element is moved distally away from the open end of the cavity.

The aerosol generating device may further comprise a rotation element coupled to the capture element, such as via the shaft. The rotation element is configured to rotate the capture element. Any suitable rotation element may be employed. For example, the rotation element may comprise a mechanical rotation element or an electromechanical rotation element. For example, the rotation element may comprise a recoil spring or other suitable wound element. In another example, the rotation element may comprise a motor, such as a screw motor.

If the aerosol generating device comprises a motor for rotation and advancement of the capture element in the cavity of the housing, the device may comprise a user activatable button that may reverse the motor to reset the capture element for use with a fresh aerosol generating article.

The device may further comprise an additional button. The additional button is a user activatable button coupled to the rotation element. This button may be termed the "activation button". Actuation of the activation button may activate the rotation element, which causes rotation of the capture element and may cause longitudinal advancement of the capture element in the cavity. Preferably, actuation of the activation button causes the capture element to rotate a predetermined amount, such as an amount substantially equal to an amount that the heating element extends around a circumference of the cavity. Preferably, actuation of the activation button also causes longitudinal advancement of the capture element in the cavity by a predetermined amount. For example, the longitudinal advancement may be such that after one complete revolution of the capture element, the capture element longitudinally advances in the cavity a distance substantially equal to the length of the heating element.

The activation button coupled to the rotation element may also be coupled to electronics controlling the heater, such that activation of the activation button to activate the rotation element may also activate the heating element. Preferably, a user will actuate the activation button prior to each puff to cause movement of the aerosol generating article restrained in the capture element to move such that a fresh, unused portion of the article is exposed to the heater, which is also activated by actuation of the activation button.

In some examples, a separate button may be employed to activate or deactivate the heating element.

As used herein, an actuatable "button" is any element to which force may be applied to activate or actuate an element coupled to the button. For example, the button may comprise a wheel, slide, pivoting member, depressible member, or the like. The button, or a portion of the button, is preferably accessible to a user external to the housing.

An aerosol generating device according to the present invention may comprise any suitable heating element. The heating element may comprise a resistive heating element, an inductive heating element, or a combination thereof. Preferably, the heating element comprises a resistive heating element. The device may comprise any suitable number of heating elements. Preferably, the device comprises only a single heating element.

The heating element may comprise a resistive heating component, such as one or more resistive wires or other resistive elements. The resistive wires may be in contact with a thermally conductive material to distribute heat produced over a broader area. Examples of suitable conductive materials include aluminium, copper, zinc, nickel, silver, and combinations thereof. For purposes of this disclosure, if resistive wires are in contact with a thermally conductive material, both the resistive wires and the thermally conductive material are part of the heating element.

In some examples, a heating element comprises an inductive heating element. For example, the heating element may comprise a susceptor material that forms a surface of the cavity or is exposed to the cavity. As used herein, the term 'susceptor' refers to a material that is capable to convert electromagnetic energy into heat. When located in an alternating electromagnetic field, typically eddy currents are induced and hysteresis losses may occur in the susceptor causing heating of the susceptor. As the susceptor is located in thermal contact or close thermal proximity with the aerosol generating substrate in the aerosol generating article, the substrate is heated by the susceptor such that an aerosol is formed.

The susceptor may be formed from any material that can be inductively heated to a temperature sufficient to generate an aerosol from the aerosol-forming substrate. Preferred susceptors comprise a metal or carbon. A preferred susceptor may comprise or consist of a ferromagnetic material, for example ferritic iron, a ferromagnetic alloy, such as ferromagnetic steel or stainless steel, and ferrite. A suitable susceptor may be, or comprise, aluminium.

Preferred susceptors are metal susceptors, for example stainless steel. However, susceptor materials may also comprise or be made of graphite, molybdenum, silicon carbide, aluminum, niobium, Inconel alloys (austenite nickel-chromium-based superalloys), metallized films, ceramics such as for example zirconia, transition metals such as for example Fe, Co, Ni, or metalloids components such as for example B, C, Si, P, Al.

A susceptor preferably comprises more than 5%, preferably more than 20%, preferably more than 50% or 90% of ferromagnetic or paramagnetic materials. Preferred susceptors may be heated to a temperature in excess of 250 degrees Celsius. Suitable susceptors may comprise a non-metallic core with a metal layer disposed on the non-metallic core, for example metallic tracks formed on a surface of a ceramic core.

If the heating element comprises a susceptor, the device may also comprise one or more induction coils configured to induce eddy currents and/or hysteresis losses in the susceptor material, which results in heating of the susceptor material.

The aerosol generating device may comprise control electronics operably coupled to the resistive heating element or induction coil. The control electronics are configured to control heating of the heating element. The control electronics may be internal to the housing.

The control electronics may be provided in any suitable form and may, for example, include a controller or a memory and a controller. The controller may include one or more of an Application Specific Integrated Circuit (ASIC) state machine, a digital signal processor, a gate array, a microprocessor, or equivalent discrete or integrated logic circuitry. Control electronics may include memory that contains instructions that cause one or more components of the circuitry to carry out a function or aspect of the control electronics. Functions attributable to control electronics in this disclosure may be embodied as one or more of software, firmware, and hardware.

The electronic circuitry may comprise a microprocessor, which may be a programmable microprocessor. The electronic circuitry may be configured to regulate a supply of power. The power may be supplied to the heater element or induction coil in the form of pulses of electrical current.

If the heating element is a resistive heating element, the control electronics may be configured to monitor the electrical resistance of the heating element and to control the supply of power to the heating element depending on the electrical resistance of the heating element. In this manner, the control electronics may regulate the temperature of the resistive element.

If the heating components comprise an induction coil and the heating element comprises a susceptor material, the control electronics may be configured to monitor aspect of the induction coil and to control the supply of power to the induction coil depending on the aspects of the coil such as described in, for example, WO 2015/177255. In this manner, the control electronics may regulate the temperature of the susceptor material.

The aerosol generating device may comprise a temperature sensor, such as a thermocouple, operably coupled to the control electronics to control the temperature of the heating elements. The temperature sensor may be positioned in any suitable location. For example, the temperature sensor may be configured to insert into the aerosol generating substrate or in contact or proximity with the heating element. The sensor may transmit signals regarding the sensed temperature to the control electronics, which may adjust heating of the heating elements to achieve a suitable temperature at the sensor.

Regardless of whether the aerosol generating device includes a temperature sensor, the device is preferably configured to heat an aerosol generating substrate of an aerosol generating article received in the cavity to an extent sufficient to generate an aerosol without combusting the aerosol generating substrate.

The control electronics may be operably coupled to a power supply, which may be internal to the housing. The aerosol generating device may comprise any suitable power supply. For example, a power supply of an aerosol generating device may be a battery, or set of batteries. The batteries maybe rechargeable, as well as removable and replaceable. Any suitable battery may be used.

The heating element is in communication with the cavity of the housing. Preferably, the heating element is disposed in the housing such that a surface of the heating element is exposed to the interior of the cavity. The heating element preferably extends less than 360 degrees around a circumference of the cavity. For example, the heating element may extend from about 5 degrees to about 180 degrees around the circumference of the cavity. Preferably, the heating element extends from about 10 degrees to about 120 degrees, or about 20 degrees to about 90 degrees, around the circumference of the cavity. More preferably, the heating element extends between about 30 degrees and about 60 degrees around the circumference of the housing.

By way of example, if the heating element extends 45 degrees around the circumference of the cavity and rotation of the capture element is configured to move in increments corresponding to this heating element, then eight partial rotations, each of 45 degrees, of the capture element will result in a complete rotation of the capture element. In this way, the full circumference of the cavity is heated in sequential portions.

Preferably, after each complete rotation of the capture element, the capture element longitudinally advances in the cavity a distance about equal to the length of the heating element. The capture element may be configured to rotate fully around the circumference of the cavity, therefore exposing the full circumference of an aerosol generating article to the heater, before a single step of longitudinal motion equal to the length of the heating element. Preferably, the longitudinal movement is simultaneous with each rotation, such that the capture element experiences spiral movement. In this way, the cumulative longitudinal movement following a full rotation of the capture element is about equal to the length of the heating element.

The heating element may have any suitable length. Preferably, the heating element extends less than the length of the cavity. For example, the heating element may be about one-fifth to about one-half of the length of the cavity. Preferably, the heating element is positioned proximate the open end of the housing.

By way of example, if the heating element is one-third the length of the cavity and the capture element is indexed relative to the length of the cavity such that the capture element advances a distance equal to the length of the heating element each full rotation, then the capture element may fully rotate three times before the capture element advances beyond the heating element.

Indexing of the movement of the capture element to the heating element, both longitudinally and rotationally, may determine the number of fresh puffs a user may take from an aerosol generating article used with the device. For example, if the heating element extends around 90 degrees of the circumference of the cavity of the housing and has a length that is one-third of the housing and if movement of the capture element is indexed to the heating element, then a user may take 12 fresh puffs, four puffs for each full rotation for three full rotations, until the capture element and aerosol generating article have advanced beyond a point at which the aerosol generating article may be effectively heated by the heating element.

Any suitable aerosol generating article may be used with an aerosol generating device according to the present invention. The aerosol generating article may have a mouth end for placement in a user's mouth and an opposing second end distal to the mouth end. The aerosol generating article comprises an aerosol generating substrate between the mouth end and the second end.

The aerosol generating article may comprise any suitable aerosol generating substrate capable of releasing volatile compounds when heated. The aerosol-generating substrate may comprise nicotine. The nicotine containing aerosol-generating substrate may comprise a nicotine salt matrix. The aerosol-generating substrate may comprise plant-based material. The aerosol-generating substrate may comprise tobacco, and preferably the tobacco-containing material contains volatile tobacco flavor compounds, which are released from the aerosol-generating substrate upon heating.

The aerosol-generating substrate may comprise homogenized tobacco material. Homogenized tobacco material may be formed by agglomerating particulate tobacco. Where present, the homogenized tobacco material may have an aerosol-former content of equal to or greater than 5% on a dry weight basis, and preferably between greater than 5% and 30% by weight on a dry weight basis.

The aerosol-generating substrate may alternatively or additionally comprise a non-tobacco-containing material. The aerosol-generating substrate may comprise homogenized plant-based material.

The aerosol-generating substrate may comprise, for example, one or more of: powder, granules, pellets, shreds, spaghettis, strips or sheets containing one or more of: herb leaf, tobacco leaf, fragments of tobacco ribs, reconstituted tobacco, homogenized tobacco, extruded tobacco and expanded tobacco.

The aerosol-generating substrate may comprise at least one aerosol-former. The aerosol-former may be any suitable known compound or mixture of compounds that, in use, facilitates formation of a dense and stable aerosol and that is substantially resistant to thermal degradation at the operating temperature of the aerosol-generating device. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Particularly preferred aerosol formers are polyhydric alcohols or mixtures thereof, such as triethylene glycol, 1,3-butanediol and, most preferred, glycerine. The aerosol-forming substrate may comprise other additives and ingredients, such as flavorants. The aerosol-generating substrate preferably comprises nicotine and at least one aerosol-former. In a particularly preferred embodiment, the aerosol-former is glycerine.

The aerosol-generating substrate may be provided on or embedded in a thermally stable carrier. In a preferred embodiment, the carrier is a tubular carrier having a thin layer of the solid substrate deposited on its inner surface, or on its outer surface, or on both its inner and outer surfaces. Such a tubular carrier may be formed of, for example, a paper, or paper like material, a non-woven carbon fiber mat, a low mass open mesh metallic screen, or a perforated metallic foil or any other thermally stable polymer matrix. Alternatively, the carrier may take the form of powder, granules, pellets, shreds, spaghettis, strips or sheets.

The carrier may be a non-woven fabric or fiber bundle into which tobacco components have been incorporated. The non-woven fabric or fiber bundle may comprise, for example, carbon fibers, natural cellulose fibers, or cellulose derivative fibers.

The aerosol generating substrate is preferably circumscribed by a wrapper, such as a cigarette paper wrapper.

The aerosol generating article may comprise a filter upstream of the aerosol generating substrate. For example, the filter may be proximate the mouth end of the aerosol generating article, Any suitable filter, such as cellulose acetate tow, may be used. The filter may be wrapped in plug wrap. The filter may be coaxially aligned with a rod of aerosol generating substrate, and the filter and rod may be held together with, for example, tipping paper.

Preferably, the aerosol generating article is cylindrical and the cavity of the aerosol generating device is cylindrical.

Reference will now be made to the drawings, which depict one or more aspects described in this disclosure. However, it will be understood that other aspects not depicted in the drawings fall within the scope and spirit of this disclosure. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. The figures are presented for purposes of illustration and not limitation. Schematic drawings presented in the figures are not necessarily to scale.

Referring now to FIG. 1, a schematic perspective view of an example of an aerosol generating device 100 and an aerosol generating article 200 inserted into the device 100. The device 100 includes a housing 110 that has an open end and forms a cavity in communication with the open end. The cavity is configured to receive the aerosol generating article 200. The device includes a first button 122, or activating button, for activating a capture element (not shown) and which may also activate a heating element (not shown). The device 100 further includes a second button 124, or disengaging button, which may be actuated to reset the capture element for use with a fresh aerosol generating article 200.

Insertion of the aerosol generating article 200 into the cavity causes an end of the article to be restrained in the capture element. For purposes of the present disclosure, the article is restrained relative to the capture element if the article is not free to rotate relative to the capture element.

Actuation of button 122 causes the capture element to advance in the cavity in a spiral manner, and thus causes the aerosol generating article to move through the cavity in a spiral manner. In the embodiment shown in the Figures, the aerosol generating article moves proximally through the cavity, towards the open end, in increments during use.

The heating element is preferably in contact with the aerosol generating article 200 and is configured to heat aerosol generating substrate in the article 200 to generate aerosol, which can be inhaled by a user through the mouth end of the article 200, which extends from the cavity beyond the open end of the cavity.

Once a portion of the aerosol generating article 200 has been heated, the article 200 may be moved so that a fresh portion of the article 200 may be placed adjacent to the heater for heating. Depressing button 122 causes movement of the capture element and, thus, the article 200.

Figure 2:
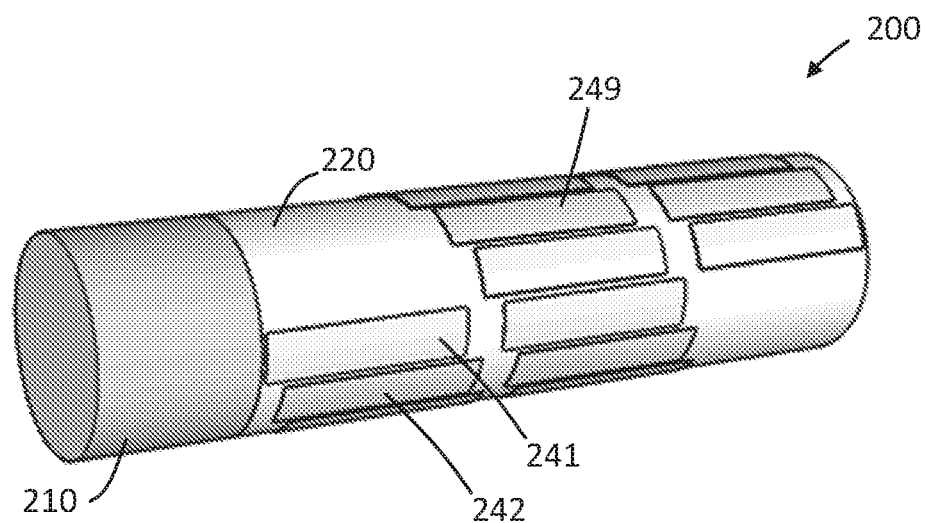
FIG. 2 is a schematic perspective view of an aerosol generating article of the type to be used with the device of the present invention.

Referring now to FIG. 2, a schematic perspective view of an example of an aerosol generating article 200 that has undergone multiple rounds of sequential heating by, for example, a device 100 depicted in FIG. 1 is shown. The article 200 includes a mouth end 210, which may comprise a filter, and a rod 220 downstream of the mouth end 210. The rod 220 contains aerosol generating substrate. The rectangular boxes on the article (e.g., 241, 242, and 249) indicate sequentially heated portions of the rod 220. For example, portion 241 may be the first portion to be heated, portion 242 may be the second portion to be heated, and portion 249 may be the ninth portion to be heated. Depression of, for example, button 122 shown in FIG. 1 may cause the aerosol generating article 200 to move relative to the heating element of the device 100 shown in FIG. 1 so that a subsequent unused portion of the rod 220 may be heated. When the article 200 is fully used, the article may be removed from the device and a fresh article may be inserted into the device.

Figure 3A:
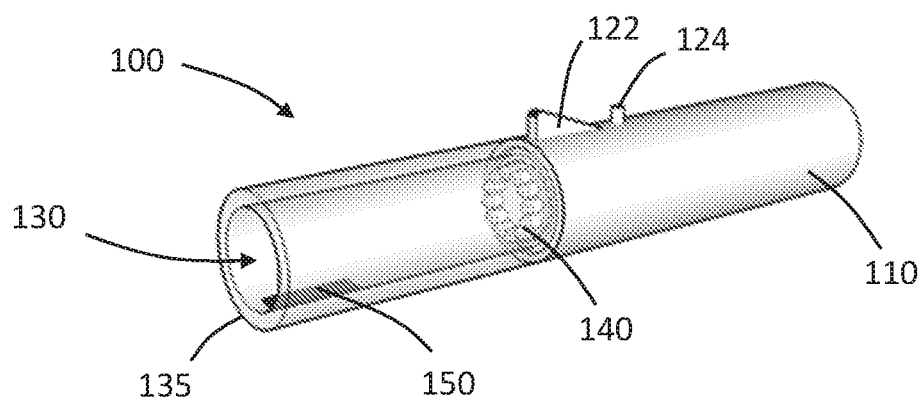
FIG. 3A is a schematic perspective view of an aerosol generating device according to the present invention, in the starting position.
Figure 3B:
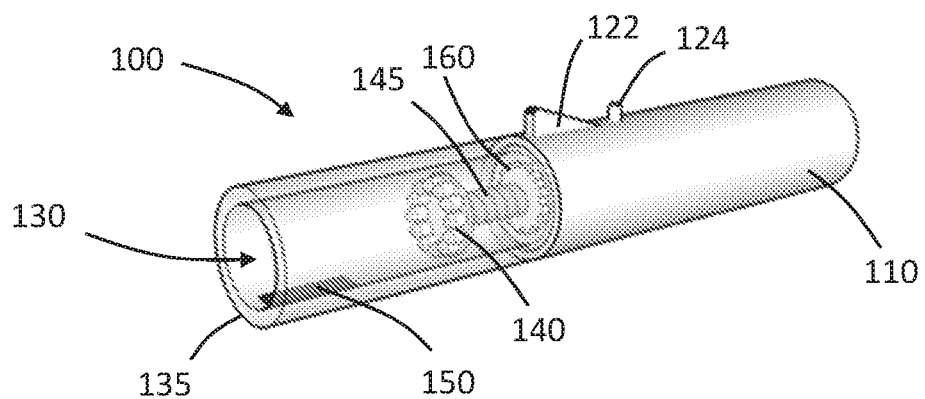
FIG. 3B is a schematic perspective view of an aerosol generating device according to the present invention, in an advanced position.

The device 100 depicted in FIGS. 3A-B has a housing 110 having an open end 135. The housing 110 defines a cavity 130 in communication with the open end. The cavity 130 and open end 130 are configured to receive an aerosol generating article, such as the article 200 shown in FIG. 2. On insertion into the cavity, the article is restrained by capture element 140, which is disposed in the cavity 130.

The capture element 140 is coupled to a threaded shaft 145, which is coupled to rotation element 160. The rotation element 160 is operably coupled to button 122. The rotation element 160 may comprise, for example, a recoil spring or a screw motor.

Actuation of button 122 by a user causes the rotation of the rotation element 160, which causes the threaded shaft 145 and the capture element 140 to advance proximally in the cavity 130 in a spiral manner. FIG. 3A shows the capture element 140 in the starting or reset position. FIG. 3B shows the capture element 140 in a proximally advanced position.

The device 100 includes a heating element 150 disposed in or exposed to the cavity 130 for heating an aerosol generating substrate of an aerosol generating article, when the article is received in the cavity 130 and restrained by the capture element 140. The heating element 150 extends less than the circumference of the cavity 130. In the depicted embodiment, the heating element 150 extends about one-tenth of the circumference of the cavity 130. In other words, the heating element 150 extends about 36 degrees of the circumference of the cavity 130.

Figure 4:
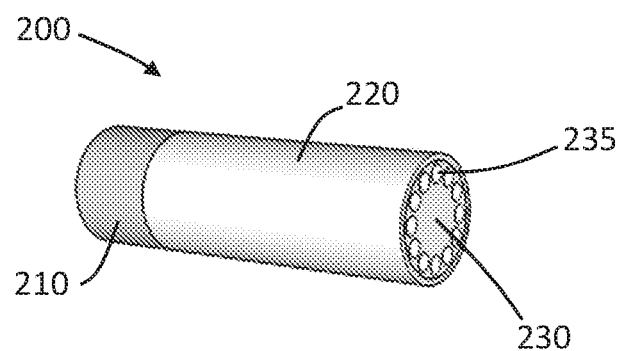
FIG. 4 is a schematic perspective view of an aerosol generating article of the type to be used with the device of the present invention.

Referring now to FIG. 4, a schematic perspective view of an example of an aerosol generating article 200 is shown. The article 200 includes a mouth end 210 and a second end opposing the mouth end. The article 200 comprises a rod 220 containing aerosol generating substrate upstream of the mouth end 210. The second end comprises a plate 230 comprising features 235 configured to interact with features of the capture element of the aerosol generating device such that the article 200 is restrained by the capture element when the article 200 is inserted into the cavity of the device. For example, the plate 230 may comprise detents or holes 235 as depicted in FIG. 4 and the capture element may include detents or protrusions (e.g. as depicted in FIGS. 3A-B) to mate with the holes 235.

Figure 5A:
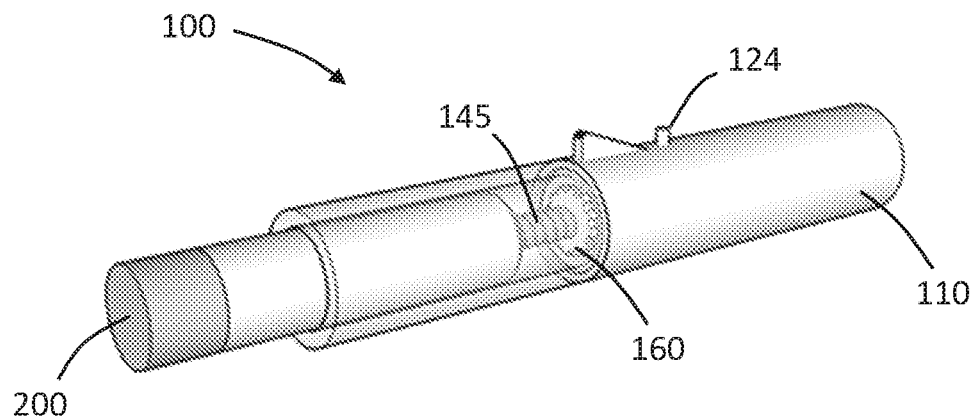
FIG. 5A is a schematic perspective view of an aerosol generating article retained within an aerosol generating device of the present invention in an advanced position.
Figure 5B:
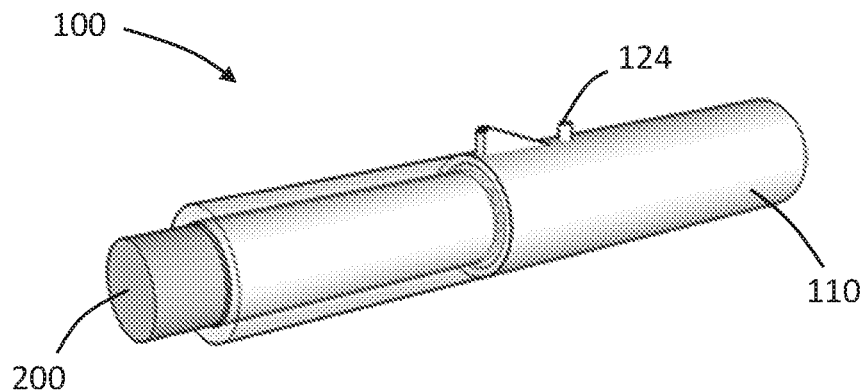
FIG. 5B is a schematic perspective view of an aerosol generating article retained within an aerosol generating device of the present invention in a starting position.

Referring now to FIGS. 5A-B, schematic perspective views of an example of a device 100 and aerosol generating article 200 for use with the device 100 are shown. FIGS. 5A-B illustrate resetting of the device 100, more specifically the capture element (not shown in FIGS. 5A-B due to the presence of the article 200). In the depicted example, actuation of button 124 allows for the capture element and the threaded shaft 145 to be pushed distally in the cavity by inserting the article 200 against the capture element until the device is reset (FIG. 5B).

Depressing button 124 may cause a thread engagement element of rotation element 160 to disengage from a thread of the threaded shaft 145 to allow the capture element and threaded shaft 145 to be pushed distally within the cavity.

Figure 6A:
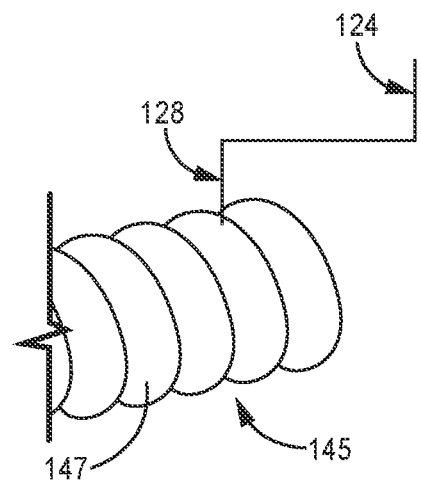
FIG. 6A is a schematic perspective view of a portion of the threaded shaft of the device with a schematic view of a disengaging button in an engaged position.
Figure 6B:
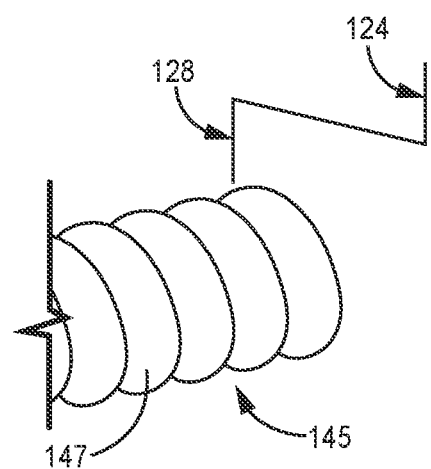
FIG. 6B is a schematic perspective view of a portion of the threaded shaft of the device with a schematic view of a disengaging button in a disengaged position.

For example and with reference to FIGS. 6A-B, a schematic perspective view of a portion of the threaded shaft 145 with a schematic side view of button 124 and thread engagement element 128 are shown. Other components of the aerosol generating device are not shown. In FIG. 6A, the button 124 is not actuated or depressed, and the thread engagement element 128 is engaged with the thread 147 of the threaded shaft 145. In FIG. 6B, the button 124 is actuated or depressed, and the thread engagement element 128 is disengaged from the thread 147 of the threaded shaft 145 to allow the threaded shaft to move freely and return to its starting or reset position. Upon release of button 124, the engagement element 128 may re-engage with the thread 147 so that the device may be ready for use.

In embodiments, where the rotation element comprises a motor, depression of the button to reset that capture element and the threaded shaft may cause reversal of the motor rather than disengagement of the engagement element. In other words, the capture element and threaded shaft may be spirally rewound to the starting or reset position.

Figure 7:
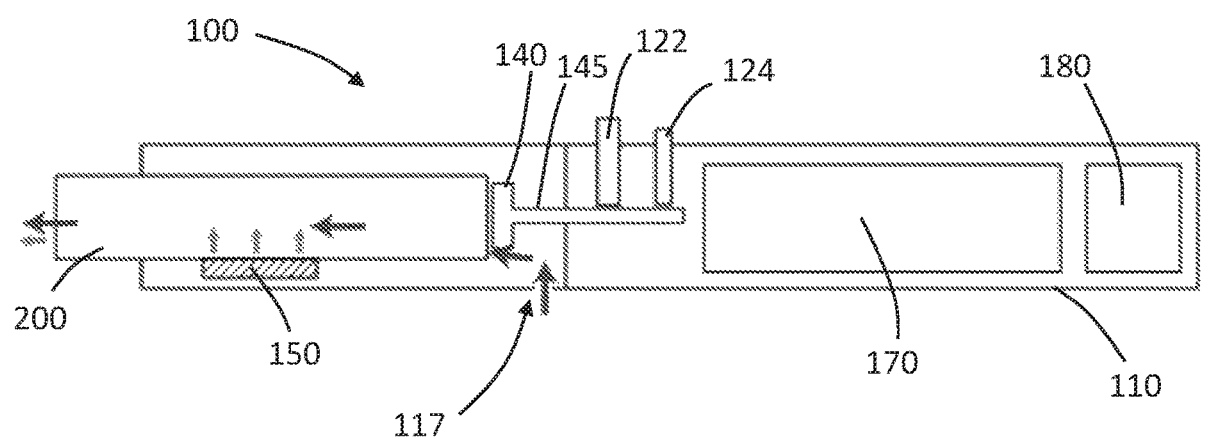
FIG. 7 is a schematic cut-through view of an aerosol generating article retained within an aerosol generating device of the present invention.

Referring now to FIG. 7, a schematic longitudinal sectional view of a device 100 and article 200 is shown. Reference is made to the discussion regarding FIGS. 1, 3A-B, and 5A-B above for numbered elements depicted in FIG. 7 that are not specifically discussed regarding FIG. 7. The device 100 includes a battery 170 operably coupled to control electronics 180, which are operably coupled to heating element 150.

Air and aerosol flow through the article 200 are depicted in FIG. 7. As shown, the housing 110 of the device 100 may comprise one or more openings 117 in communication with the cavity in which the article 200 is received. As a user draws on the mouth end of the article 200 air may enter the cavity through the openings 117 and flow through the article 200. Air flow is indicated by the larger arrows in FIG. 7. Aerosol is generated by heating of the aerosol generating substrate in the article 200 by the heating element 150. The aerosol may be entrained in the air and delivered to the mouth end of the article 100 for inhalation by a user. Aerosol is depicted by the smaller arrows in FIG. 7.

All scientific and technical terms used herein have meanings commonly used in the art unless otherwise specified. The definitions provided herein are to facilitate understanding of certain terms used frequently herein.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits under certain circumstances. However, other embodiments may also be preferred under the same or other circumstances. Furthermore, the recitation of one or more preferred embodiments does not imply that other embodiments are not useful, and is not intended to exclude other embodiments from the scope of the disclosure, including the claims.

Any direction referred to herein, such as "top," "bottom," "left," "right," "upper," "lower," and other directions or orientations are described herein for clarity and brevity are not intended to be limiting of an actual device or system. Devices and systems described herein may be used in a number of directions and orientations.

The embodiments exemplified above are not limiting. Other embodiments consistent with the embodiments described above will be apparent to those skilled in the art.

The invention claimed is:

1. An aerosol generating device, comprising:
a housing having an open end, wherein the housing forms a cavity in communication with the open end for receiving an aerosol generating article;
a rotatable capture element disposed in the cavity and operable to retain the aerosol generating article within the cavity, wherein the rotatable capture element is longitudinally movable within the cavity; and
a heating element in communication with the cavity, wherein the heating element is operable to heat the aerosol generating article retained by the capture element within the cavity; and,
wherein rotation of the capture element causes the aerosol generating article retained by the capture element to spirally move relative to the heating element.

2. The aerosol generating device according to claim 1, further comprising a rotation element coupled to the capture element and configured to rotate the capture element.

3. The aerosol generating device according to claim 2, wherein the rotation element comprises a recoil spring or a motor.

4. The aerosol generating device according claim 2, further comprising a user actuatable button coupled to the rotation element, wherein actuation of the button activates the rotation element and causes the capture element to rotate.

5. The aerosol generating device according to claim 1, further comprising a shaft coupled to the capture element.

6. The aerosol generating device according to claim 5, wherein the shaft comprises a thread, and wherein the device further comprises a thread engagement element configured to engage the thread of the shaft.

7. The aerosol generating device according to claim 6, wherein rotation of the shaft while engaged by the thread engagement element causes rotation of the capture element and causes the capture element to move longitudinally in the cavity.

8. The aerosol generating device according to claim 6, wherein the thread engagement element is actuatable to disengage the thread.

9. The aerosol generating device according to claim 1, wherein the capture element is configured to move in increments of a predetermined amount.

10. The aerosol generating device according to claim 9, wherein the predetermined amount of movement of the capture element includes a rotational increment and a longitudinal increment.

11. The aerosol generating device according to claim 10, wherein the rotational increment of the predetermined movement of the capture element is an amount substantially equal to an amount that the heating element extends around a circumference of the cavity.

12. The aerosol generating device according to claim 11 wherein the longitudinal increment of the predetermined movement of the capture element is an amount substantially equal to the length that the heating element extends along the length of the cavity, divided by the number of rotational increments required for a full rotation.

13. The aerosol generating device according to claim 1, wherein the capture element moves with spiral movement within the cavity.

14. The aerosol generating device according to claim 1, wherein the heater element heats adjacent portions of an aerosol generating article retained by the capture element in sequence.

15. The aerosol generating system comprising:
an aerosol generating device according to claim 1; and
the aerosol generating article comprising:
a mouth end and a distal end distal to the mouth end;
the aerosol generating substrate between the mouth end and the distal end; and
a plate at the distal end, wherein the plate comprises a feature configured to engage with the rotatable capture element of the aerosol generating device.

* * * * *